United States Patent [19]

Whipple

[11] Patent Number: 4,880,414
[45] Date of Patent: Nov. 14, 1989

[54] CATHETER ATTACHMENT SYSTEM

[75] Inventor: Gary R. Whipple, South Attleboro, Mass.

[73] Assignee: Pharmacia Nu Tech, Walpole, Mass.

[21] Appl. No.: 140,026

[22] Filed: Dec. 31, 1987

[51] Int. Cl.⁴ ............................................. A61M 25/00
[52] U.S. Cl. ..................................... 604/283; 285/243
[58] Field of Search .................... 604/283, 280, 257; 285/243, 242, 255

[56] References Cited

U.S. PATENT DOCUMENTS

| | | | |
|---|---|---|---|
| 3,724,882 | 4/1973 | Dehar | 285/243 |
| 3,958,557 | 5/1976 | Sharp et al. | 604/280 |
| 4,417,890 | 11/1983 | Dennehey et al. | 604/905 |
| 4,564,222 | 1/1986 | Loker et al. | 285/243 |
| 4,635,973 | 1/1987 | Sauer | 285/243 |
| 4,723,948 | 2/1988 | Clark et al. | 604/283 |

Primary Examiner—C. Fred Rosenbaum
Assistant Examiner—Kathleen A. Daley
Attorney, Agent, or Firm—Nutter, McClennen & Fish

[57] ABSTRACT

This connection system has particular application to releasably securing a flexible elastic catheter to a rigid portal outlet stem received in the catheter lumen. The system includes a radial enlargement on the outlet stem and a retainer sleeve that slidably encircles the stem. The sleeve is slidable along the stem between a clamping position wherein it tightly engages around the stem enlargement and the segment of catheter encircling same at a circular contact surface and a release position wherein it is spaced from the catheter segment. The system assures a secure, fluid-tight connection of the catheter to the stem and provides strain relief for the catheter.

16 Claims, 1 Drawing Sheet

CATHETER ATTACHMENT SYSTEM

This invention relates to a catheter. It relates more particularly to improved means for connecting a flexible infusion catheter to a source of infusate.

BACKGROUND OF THE INVENTION

The treatment of certain diseases of the human body often requires the short-term or long-term infusion of drugs, blood products or nutritional or other fluids into the patient's venous or arterial system or peritoneal or epidural space. While such fluids can be administered extracorporeally by transcutaneous injection, in some cases, as when a particular patient's regime requires repeated access for drug infusion, or where infection is of acute concern, it is desirable to provide the patient with a totally implanted infusion system.

Such a system includes an injection portal which is an infusate chamber implanted subcutaneously and placed on the chest wall or other convenient body location. The portal is fitted with a needle-penetrable septum which is located directly under the skin by which drugs or other fluids may be introduced into the portal by transcutaneous injection through the septum. The portal has a fluid outlet tube or stem which is connected to one end of a flexible catheter which leads to the infusion site which is usually a blood vessel or particular body cavity, e.g., the peritoneal cavity. Since the system is completely implanted, it reduces the risk of infectious complications and allows drug infusion which is targeted to the specific patient malady. Even though the delivery system may be implanted for a long period, the patient remains ambulatory and can be treated on an out-patient basis and the system does not interfere with the normal daily activities of the patient.

A similar prosthesis can be used to draw blood from an artery or vein for blood sampling purposes.

Since an implantable device of this type may remain in the patient's body for many months, it is essential that the connection or attachment of the catheter to the portal remain secure and fluid-tight during the entire period of implantation. If the connection should fail or if there should be an infusate leak at that location, the infusate dose required to treat the patient which is injected into the portal will not be conducted to the targeted infusion site in the patient's body. Rather, some or all of the infusate will be dispensed at the site of the portal and could cause complications at that body location. In this connection, it should be appreciated that after a drug delivery system is implanted, the catheter is subjected to various stresses and strains due to movements of the patient's body, weight changes, etc. These are reflected in tensile and twisting forces at the connection of the catheter to the portal outlet which tend to upset the integrity of that union.

In an attempt to avoid this leakage problem and the attendant complications, various steps have been taken to strengthen the connection between the catheter and the portal. These include the providing of raised circular rings or ribs on the portal outlet stem over which the catheter wall is stretched. These lines of localized resilient engagement resist sliding movements of the catheter from the portal stem. In some systems, the connection is made somewhat more secure by providing a locking ring or bushing which encircles the catheter and is releasably captured on the catheter segment engaged on the portal stem by the raised ribs thereon.

We have found, however, that these prior catheter connections are not entirely satisfactory. Sometimes the tensile forces exerted on the catheter due to movements of the patient still suffice to separate the catheter from the portal or to tear the catheter at that point of connection because of a poor distribution of stresses on the catheter wall. Certain prior systems are disadvantaged in that it is quite difficult to connect the catheter to the portal outlet stem. This is because that stem is often very small (e.g. 1 mm OD), and to make the connection, the stem must be threaded into the end of the catheter lumen which is itself equally small. Furthermore, when inserting the portal stem into the catheter, if one is not quite careful, the catheter will be punctured by the end of the stem which, being so small, constitutes a sharp point. Certain prior systems are disadvantaged in that they have loose parts that are hard to handle and can be lost. This is because the system requires a separate lock that must be put on the catheter before the connection to the stem is made. These lock parts are small and easy to drop or lose.

In addition, it should be kept in mind that it may be necessary to disconnect the catheter from an already implanted injection portal in the event that the catheter has to be replaced for one reason or another. For example, it sometimes happens that the catheter lumen becomes clogged by clots or other debris. Therefore, it is desirable that any connection between the catheter and the portal be separable from the portal with a minimum amount of effort and finger manipulation by the surgeon who must make that repair subcutaneously. The prior catheter connection or attachment systems of which applicant is aware, do not facilitate such ready connection and disconnection of the catheter to and from the portal.

SUMMARY OF THE INVENTION

Accordingly, the present invention aims to provide an improved catheter attachment system.

Another object of the invention is to provide a catheter attachment system which is very strong, yet which can be released quite easily if the need should arise.

Another object of this invention is to provide a catheter connection system which has no loose part that can be lost.

Another object of the invention is to provide a catheter connection which is specially adapted for use in an implantable infusion system for joining the catheter to an injection portal.

Yet another object of the invention is to provide an attachment system of this type which minimizes localized stresses on the catheter in the region of the attachment.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

The catheter attachment or connection system of interest here may be used in any application where it is necessary to releasably connect the end of a flexible resilient catheter or other tube to a stem, tube or rod by inserting the stem, tube or rod into the end of the catheter. Since the invention has particular application to the connection of a catheter to the outlet stem of an implantable injection portal, we will describe the invention in this context. It should be understood, however, that the invention may be applied to other applications where similar flexible tube-to-rigid tube connections are required.

Briefly, the present attachment system involves the coaction and cooperation of a flexible resilient catheter, a relatively rigid stem or tube onto which the catheter is slid to effect the connection and a specially designed, locking retainer which encircles the stem and catheter on the stem. The system provides strain relief to the catheter and minimizes localized stresses on the catheter due to tensile and other forces exerted on the catheter in use.

The stem component of the system is formed with an axially symmetric radial enlargement. This enlargement takes the form of a three-dimensional bulb located adjacent to the distal end of the stem. The distal end segment of the stem beyond the enlargement has a diameter which is approximately the same as the diameter of the lumen in the catheter being connected to the stem with the enlargement being appreciably larger than that lumen.

When the catheter, which is the second component of the system, is slid onto the stem, the elastic wall of the catheter stretches outward as required to accommodate the larger diameter stem enlargement. Thus, when the end segment of the catheter has received the full extent of the stem, the catheter resiliently engages the outer surface of the stem and conforms closely to the enlargement thereof.

The third component of my connection system, namely the retainer, is a sleeve or ring which loosely encircles the proximal end segment of the portal stem. The sleeve is free to move back and forth along the stem, but it cannot come off the stem due to its engagement with a flange adjacent to the proximal end of the stem. When the catheter is slid onto the stem over the stem enlargement it is guided into the sleeve until the end of the catheter butts against the stem flange. When that sleeve is slid outward along the stem, the sleeve captures the catheter against the stem enlargement.

As will be described shortly in greater detail, when the retainer component of my connection system is seated on the portal stem so that it captures the catheter thereon, there results a very secure connection of the catheter to the stem. Even very strong pulling, twisting and bending forces exerted on the catheter are unable to disconnect the catheter from the stem or to break the fluid-tight integrity of that connection. Actually, as we will see, such forces enhance that connection.

The catheter connection system described here is also quite easy and inexpensive to manufacture, being composed of simple metal parts which can be fabricated in quantity at minimum cost. Also, the connection is easy to make and to release, even if that needs to be done in the case of an injection portal already implanted in the body. In other words, the present apparatus facilitates sliding a catheter onto the end of a portal outlet stem and into the locking sleeve to secure the catheter to the stem with no loose parts. Also, simple finger movements suffice to manipulate the connector's locking ring to release the catheter from the stem. Consequently, the present attachment system could be used conveniently wherever it is necessary to releasably connect a flexible catheter or other tube to a relatively rigid rod or stem.

BRIEF DESCRIPTION OF THE DRAWING

For a fuller understanding of the nature and objects of the invention, reference should be had to the following detailed description taken in connection with the accompanying drawing, in which.

DESCRIPTION OF THE PREFERRED EMBODIMENT

Figure 1:
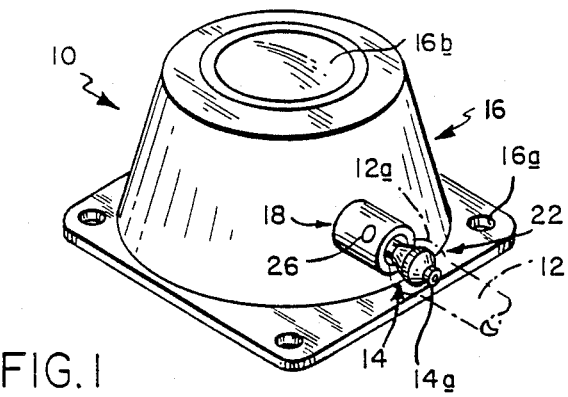
FIG. 1 is an isometric view of an implantable injection portal incorporating a catheter attachment system made in accordance with this invention.

Referring to FIG. 1 of the drawing, my catheter attachment system, indicated generally at 10, is shown connecting the proximal end of a catheter 12 to the tubular outlet stem 14 of an implantable injection portal 16. The portal is made of a material such as titanium and in use it is implanted at a convenient location in the body, such as on the chest wall. This portal might be used, for example, to conduct infusate to a vein leading to the heart. Usually, small eyes 16a are provided around the base of the portal through which sutures may be passed to anchor the portal to the chest wall. The portal also includes a septem 16b composed of a suitable resilient, needle-penetrable material, such as silicone rubber.

When the portal is implanted, the septum is situated directly under the patient's skin so that infusate can be introduced into the portal by transcutaneous injection through the septum. The infusate thereupon flows through the portal outlet stem 14 to the catheter 12 whose distal end is placed at a selected infusion site in the body, such as a blood vessel or a body cavity such as the peritoneal cavity. Catheter 12 is made of a flexible, resilient biocompatible material, such as silicone rubber. The inside diameter of the catheter, which corresponds more or less to the nominal outside diameter of portal stem 14, may vary depending upon the particular application, from, say 0.5 to 3.0 mm. Likewise, the volume of the portal 16 may vary from, say, 0.4 ml to 1.0 ml.

Figure 2:
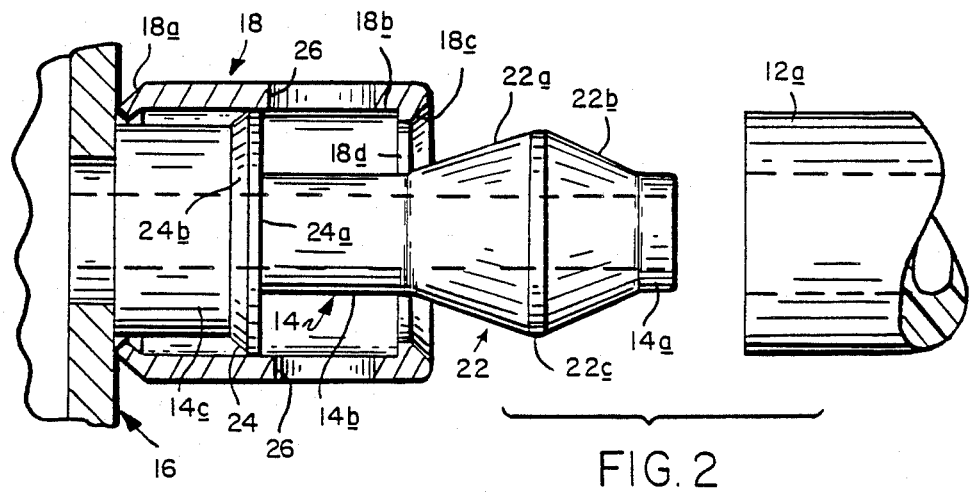
FIG. 2 is an exploded side elevational view on a much larger scale and with parts broken away showing the catheter attachment system in its unlocked position.

Referring now to FIGS. 1 and 2 of the drawing, connection system 10 is composed of three distinct parts or components. These include the proximal end segment 12a of the catheter, the portal outlet stem 14 and a special locking retainer shown generally at 18. The tubular stem 14 is formed with a radial enlargement 22 along its length. In the system embodiment depicted herein, the enlargement 22 is located adjacent to the outer or distal blunt end segment 14a of the stem 14 and it has the general form of a barrel with two back-to-back frustoconical segments 22a and 22b. The enlargement has a relatively large, rounded shoulder 22c midway along its length, i.e. between segments 22a and 22b whose diameter is appreciably larger than the inside diameter of catheter 12. The enlargement 22 tapers from that shoulder to stem end segment 14a and to a longer stem segment 14b closer to the portal 16 housing. The inner end of stem segment 14b leads to a much larger proximal stem segment 14c projecting from the wall of the portal housing. For reasons to be described later, a radial flange 24 is provided at the boundary of stem segments 14b and 14c. The flange has a radial outer or distal surface 24a and a beveled inner or proximal surface 24b. The diameter of stem segment 14a may be somewhat smaller than the inside diameter of the catheter to aid in initiating catheter engagement, i.e. in aligning the proximal end 22a of the catheter with the stem end segment 14a. The diameter of stem segment 14b is somewhat larger than the diameter of the catheter so that a fluid tight seal is produced between that segment and the catheter.

The shape of the enlargement 22 is such that the stem end segment 14a and the frustonconical segment 22b of the enlargement 22 can be introduced into the end of the catheter segment 12a for a distance corresponding to about half the enlargement diameter without extending or stretching the catheter wall. Further penetration of the stem 14 into the catheter segment 12a results in the catheter wall stretching or deforming to accommodate enlargement 22, particularly shoulder 22c. That is, the catheter 12, which is typically silicone rubber, is very resilient. Thus, when catheter segment 12a is engaged fully on stem 14 as shown in FIG. 3, i.e. with the end of the catheter engaging flange 24, due to the resiliency of the catheter material, the catheter segment assumes the exact shape of outlet stem 14, including its enlargement 22 and stem segments 14a and 14b.

Figure 3:
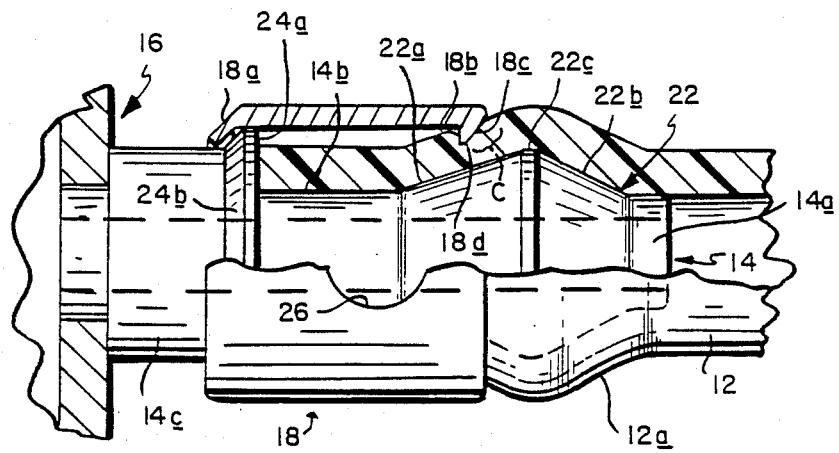
FIG. 3 is a side elevational view showing the connection system in its locked position.

As best seen in FIGS. 2 and 3, the locking retainer 18 is a generally cylindrical sleeve-like member which is slidably engaged on the stem 14. Retainer 18 is an easily fabricated, metal (e.g. titanium) or molded plastic part. The inside diameter of the retainer is slightly larger than that of stem flange 24 and its length is comparable to the combined lengths of stem segments 14b and 14c. The inner or proximal end of the retainer is necked down to form an inwardly extending circular flange or rib 18a which overhangs stem flange 24 and is oriented at more or less the same angle as the bevelled surface 24b of that flange.

The outer or distal end of retainer 18 has a reduced inner diameter that creates a circular inner rib, flange or ledge 18b on the retainer. Also, that end of the retainer is bevelled to provide a flared or bevelled surface 18c which extends from the inner edge of ledge 18b toward the outer wall of the retainer. As best seen in FIG. 2, the ledge 18b and bevelled surface 18c together produce a structure at the distal end of the retainer which, in crossection, has the general shape of an annular barb whose blunted nose 18d projects toward stem 14. When the retainer and stem are coaxial, the flare angle of surface 18c, as measured from the stem 14 longitudinal axis or centerline, is appreciably greater than that of enlargement segment 22a so that when catheter 12 is tensioned, nose 18d will bite into the catheter wall creating strong retention forces. For example, the former angle may be 45° and the latter angle 20°.

Retainer 18 is slidable along stem 14, with the stem flange 24 providing a bearing surface, between an unlocking position shown in FIG. 2 established by the engagement of the retainer flange 18a against the portal housing, wherein the retainer surface 18c and nose 18d are spaced appreciably from enlargement segment 22a and a locking position shown in FIG. 3 wherein the surface 18c and nose 18d are situated close to segment 22a, with the nose lying about halfway along the length of that segment. The stem flange 24, in addition to functioning as a stop for catheter 12 and as a bearing surface for the retainer as described above, also prevents the retainer 18 from sliding off the stem 14 by engaging the retainer flange 18a. A pair of diametrically opposite holes 26 are provided in the wall of retainer 18 to make it easier for the surgeon to see that the catheter is completely in place and abutting flange 24 inside the locking retainer.

The connection of catheter 12 to stem 14 can be made quite easily with one hand, even when the surgeon has no clear view of the connection site. To effect the connection, the surgeon grasps the end of the catheter and, feeling with his fingers, slides the catheter onto the end segment 14a of portal stem 14. He then pushes the end of the catheter over the stem enlargement 22 and into sleeve 18 until the catheter end is stopped by the stem flange 24. He can verify that the catheter is seated properly by observation through the retainer holes 26. The surgeon then pulls back gently on locking retainer 18 until the retainer nose 18d engages against and compresses the outer surface of catheter segment 12a as shown in FIG. 3. Most desirably, the inner diameter of retainer ledge or flange 18b, or more particularly of its nose 18d should be less than the diameter of enlargement shoulder 22c in which event, retainer flange 18a could be dispensed with. However, this creates manufacturing difficulties. To avoid these difficulties, the diameter of retainer nose 18d is dimensioned to be smaller than the diameter of stem enlargement 22 plus twice the wall thickness of the catheter segment stretched over that segment 14b.

When the connection is made and locked as shown in FIG. 3, it is practically impossible to pull catheter 12 from the portal stem 14. Any pulling or twisting forces applied to the catheter only serve to tighten the connection between the catheter and the stem. That is, when catheter 12 is pulled away from portal 16, it pulls retainer 18 along with it to a locking position against enlargement segment 22a at a circular area of contact C (FIG. 3). Increased tensile forces only serve to pull the retainer more tightly against segment 22a at contact surface C. Resultantly, the retainer surface 18c and nose 18d are moved closer to the frustoconical segment 22a of enlargement 22 so that nose 18d clamps or bites even more firmly into the stretched catheter wall thereby further increasing the retention forces on the catheter. Accordingly, a frustoconical catheter segment is sandwiched or compressed ever more tightly between enlargement segment 22a and the retainer surface at contact surface C, as clearly seen in FIG. 3.

That engaged and compressed segment of the catheter has a relatively large area so that the stresses on the catheter due to such pulling and twisting forces are distributed uniformly over that segment, thus avoiding localized strains in the catheter wall that might tend to promote tears or punctures in that wall. Consequently, there is very little likelihood of the catheter pulling away from the portal outlet stem 14 or tearing due to movements of the patient in which the prosthesis is implanted. Indeed, the integrity of the connection system 10 should be maintained for the entire period of implantation.

However, if it should become necessary to replace the catheter 12 for some reason, the present system 10 facilitates that as well. To remove the catheter, the surgeon simply holds the retainer 18 back or urges it toward the portal housing while pulling the catheter from stem 14. Since the retainer cannot move outward, it cannot clamp the catheter segment 12a to enlargement 22, so the catheter will pull off readily, leaving the stem 14 ready for a new catheter. Indeed, the same locking retainer and portal stem can be assembled and disassembled many times if need be.

It will be seen from the foregoing, then, that my catheter connection system establishes a reliable, releasible, fluid-tight and easily made joint or connection between the end of a catheter or other flexible tube and a rigid tube, stem or other fluid pathway. The system's locking retainer is easy to manipulate when connecting and disconnecting the catheter from the tube or stem, even if the surgeon's view is obstructed. Yet the components of the system are relatively easy and inexpensive to make so that the providing of this secure connection does not materially increase the overall cost of the injection portal or other prosthesis incorporating the invention.

What is claimed as new and desired to be secured by Letters Patent of the United States is:

1. Connection apparatus comprising
   A. a relatively rigid elongated stem, said stem having a free end, an opposite end and means defining an enlargement on the exterior surface of the stem at a selected location between said ends;
   B. a flexible elastic tube having a lumen for elastically receiving a lengthwise segment of said stem including said enlargement thereof, said enlargement having a maximum diameter appreciably larger than that of the lumen so that when said stem segment is received in the lumen, said tube is stretched conformingly around said stem enlargement; and
   C. tubular retainer means slidably received on said stem between said tube opposite end and said enlargement, said retainer means including radially inwardly extending rigid flange means at or near a distal end of said retainer means that faces said enlargement, said flange means having a fixed diameter that is less than the maximum diameter of said stem segment plus twice the wall thickness of said tube when engaged elastically on said stem segment so that when said stem segment is received in the tube lumen and said retainer means are slid toward the free end of said stem, said flange means compressively engage the elastically stretched wall of said tube at a contact surface that encircles a segment of said enlargement.

2. The connection apparatus defined in claim 1 wherein said stem segment is received in said lumen.

3. The connection apparatus defined in claim 1 wherein the distal end of said retainer means is bevelled outwardly adjacent to said flange means at a selected bevel angle.

4. The connection apparatus defined in claim 1 wherein the enlargement segment encircled by said flange means is flared at a selected flare angle.

5. The connection apparatus defined in claim 4 wherein the flare angle is less than said bevel angle as measured from the longitudinal axis of said stem.

6. The connection apparatus defined in claim 5 wherein said enlargement comprises a pair of integral generally frustoconical sections arranged base-to-base and said flange means encircle a proximal frustoconical section adjacent to said stem opposite end.

7. The connection apparatus defined in claim 6 wherein said retainer means comprise a sleeve encircling said stem and movable therealong between a first position wherein said flange means closely encircle the proximal frustoconical section and a second position wherein said flange means do not do so thereby permitting said tube to be slid onto and from said stem segment.

8. The connection apparatus defined in claim 1 wherein said flange means clamp or bite into the tube wall when they compressively engage the tube wall so that when the tube is tensioned, the resultant lengthwise movement of the tube wall along the stem pulls the retainer means further toward the free end of the stem thereby clamping the tube more tightly between said flange means and said stem enlargement.

9. The connection apparatus as defined in claim 1 and further including coacting means on said stem and said retainer means for preventing said retainer means from sliding beyond the free end of said stem.

10. The connection apparatus defined in claim 9 wherein said coacting means comprise
    A. detent means adjacent to said opposite end of the stem; and
    B. projecting means on said retainer means that project toward said stem and engage said detent means before said retainer means can slide appreciably beyond said enlargement.

11. The connection apparatus defined in claim 1 wherein
    A. said stem is generally cylindrical;
    B. said stem enlargement has a circular cross section and axial symmetry; and
    C. aid retainer means comprise a cylindrical sleeve with a radially inwardly extending circular flange at its distal end that constitutes said flange means, said flange having a minimum diameter that is not appreciably greater than the maximum diameter of said enlargement.

12. Apparatus for connecting a relatively rigid elongated stem having a free end to a flexible tube having a lumen for elastically receiving a lengthwise segment of the stem, said apparatus comprising
    A. a radial enlargement at a selected location along the stem;
    B. a generally cylindrical sleeve slidably received on the stem for releasably clamping around a flexible tube segment encircling said enlargement, said sleeve having an inner radial rigid rib or flange at its distal end facing said enlargement and whose diameter is fixed and not appreciably larger than the maximum diameter of said enlargement; and
    C. coacting means on the stem and sleeve for preventing the sleeve from sliding beyond the free end of the stem.

13. The apparatus defined in claim 12 wherein
    A. the opening into the distal end of said sleeve is flared; and
    B. said rib or flange is located at the inner end of said flare.

14. The apparatus defined in claim 13 where said enlargement is composed of a frustoconical section facing said sleeve, said section having a flare angle that is less than the flare angle of the sleeve opening as measured from the longitudinal axis of said stem.

15. The apparatus defined in claim 14 wherein the former flare angle is about half the latter flare angle.

16. The apparatus defined in claim 12 wherein the diameter of said sleeve rib or flange is less than the maximum diameter of said stem segment plus twice the thickness of the lumen wall elastically stretched around the stem segment.

* * * * *

UNITED STATES PATENT AND TRADEMARK OFFICE
CERTIFICATE OF CORRECTION

PATENT NO. : 4,880,414

DATED : November 14, 1989

INVENTOR(S) : Gary R. Whipple

It is certified that error appears in the above-identified patent and that said Letters Patent is hereby corrected as shown below:

Col. 5, line 6, replace "22a" with --segment 12a--;

Col. 5, line 12, replace "frustonconical" with --frustoconical--;

Col. 7, lines 4-5, replace "releasible" with --releasable--.

Signed and Sealed this

Seventh Day of January, 1992

Attest:

HARRY F. MANBECK, JR.

*Attesting Officer*  *Commissioner of Patents and Trademarks*